(12) United States Patent
Leeming et al.

(10) Patent No.: US 9,500,659 B2
(45) Date of Patent: Nov. 22, 2016

(54) IN VITRO ASSESSMENT OF CARDIOVASCULAR EVENTS BY ASSAY FOR NEO-EPTITOPES OF TITIN PROTEIN

(75) Inventors: Diana Julie Leeming, Espergaerde (DK); Morten Karsdal, Copenhagen (DK); Efstathios Vassiliadis, Rodovre (DK)

(73) Assignee: Nordic Bioscience A/S, Herlev (DK)

( * ) Notice: Subject to any disclaimer, the term of this patent is extended or adjusted under 35 U.S.C. 154(b) by 146 days.

(21) Appl. No.: 14/232,405

(22) PCT Filed: Jul. 6, 2012

(86) PCT No.: PCT/EP2012/063278
§ 371 (c)(1),
(2), (4) Date: May 17, 2014

(87) PCT Pub. No.: WO2013/007643
PCT Pub. Date: Jan. 17, 2013

(65) Prior Publication Data
US 2014/0295469 A1 Oct. 2, 2014

(30) Foreign Application Priority Data

Jul. 11, 2011 (GB) .................................. 1111788.4

(51) Int. Cl.
| | |
|---|---|
| *G01N 31/00* | (2006.01) |
| *G01N 33/53* | (2006.01) |
| *G01N 33/68* | (2006.01) |
| *C07K 16/18* | (2006.01) |
| *C07K 14/47* | (2006.01) |
| *G01N 33/566* | (2006.01) |

(52) U.S. Cl.
CPC ....... *G01N 33/6887* (2013.01); *C07K 14/4716* (2013.01); *C07K 16/18* (2013.01); *G01N 33/566* (2013.01); *G01N 33/6893* (2013.01); *C07K 2317/34* (2013.01); *G01N 2333/4712* (2013.01); *G01N 2800/32* (2013.01)

(58) Field of Classification Search
CPC .... A61K 38/00; A61K 39/00; G01N 33/582; G01N 22/6893; C07K 14/705; C07K 16/18
See application file for complete search history.

(56) References Cited

U.S. PATENT DOCUMENTS 9,206,464 B2 * 12/2015 Veidal ...................... C12Q 1/37

OTHER PUBLICATIONS

Tascilar et al. (Annals of Oncology 10,Suppl. 4:S107-S110, 1999).*
Tockman et al. (Cancer Research 52:2711s-2718s, 1992).*
Ali, Mam et al. Titin is a target of matrix metalloproteinase-2: implications in myocardial ischemia/reperfusion injury. Circulation 2010; vol. 122: pp. 2039-2047; entire document.
Karsdal, Ma et al. Novel combinations of Post-Translational Modification (PTM) neo-epitopes provide tissue-specific biochemical markers—are they the cause or the consequence of the disease? Clin. Biochem. 2010; vol. 43: pp. 793-804; entire document.
Vassiliadis, E et al. Clinical evaluation of a matrix metalloproteinase-12 cleaved fragment of titin as a cardiovascular-specific serological biomarker. J. Trans. Medicine 2012; vol. 10: 140; entire document.
Vassiliadis, E et al. Novel cardiac-specific biomarkers and the cardiovascular continuum. Biomarker Insights 2012; vol. 7; pp. 45-57; entire document.
Lewinter, MM et al. Cardiac titin: structure, functions and role in disease. Clin Chim Acta 2007; vol. 375: pp. 1-9; entire document.
Lewinter, MM Cardiac titin: a multifunctional giant. Circulation 2010; vol. 121: pp. 2137-2145; entire document.
Wu, Y et al. Changes in titin isoform expression in pacing-induced cardiac failure give rise to increased passive muscle stiffness. Circulation 2002; vol. 106: pp. 1384-1389; entire document.
Sutko, JL et al. Titin: an elastic link between length and active force production in myocardium. Circulation 2001; vol. 104: pp. 1585-1587; entire document.
Jaber, WA et al. Titin isoforms, extracellular matrix, and global chamber remodeling in experimental dilated cardiomyopathy: functional implications and mechanistic insight. Circ Heart Fail 2008; vol. 1: pp. 192-199; entire document.
Hein, S et al. Giant molecule titin and myocardial stiffness. Circulation 2002; vol. 106: pp. 1302-1304; entire document.
Lewinter, MM Titin isoforms in heart failure: are there benefits to supersizing? Circulation 2004; vol. 110:109-111; entire document.
Linke, WA Sense and stretchability: the role of titin and titin-associated proteins in myocardial stress-sensing and mechanical dysfunction. Cardiovasc Res 2008; vol. 77: pp. 637-648; entire document.
Chaturvedi, RR et al. Passive stiffness of myocardium from congenital heart disease and implications for diastole. Circulation 2010; vol. 121: pp. 979-988; entire document.
Thijssen, Vljl et al. Temporal and spatial variations in structural protein expression during the progression from stunned to hibernating myocardium. Circulation 2004; vol. 110: pp. 3313-3321; entire document.
Nagueh, SF et al. Altered titin expression, myocardial stiffness, and left ventricular function in patients with dilated cardiomyopathy. Circulation 2004; vol. 110: pp. 155-162; entire document.
Peng, J et al. Cardiac hypertrophy and reduced contractility in hearts deficient in the titin kinase region. Circulation 2007; vol. 115: pp. 743-751; entire document.
Linke, WA Titin stiffness in heart disease. Circulation 2003; vol. 107: e73; entire document.

(Continued)

*Primary Examiner* — Lisa Cook
(74) *Attorney, Agent, or Firm* — Benjamin Aaron Adler

(57) ABSTRACT

An immunoassay for the quantification of fragments having an N- or a C-terminal neo-epitope formed by cleavage of a titin protein by a proteinase is provided. The immunoassay includes the steps of contacting a sample with an antibody specifically binding to the N- or C-terminal neo-epitope of the fragments and determining the level of binding.

10 Claims, 2 Drawing Sheets

(56) References Cited

OTHER PUBLICATIONS

Neagoe, C et al. Titin isoform switch in ischemic human heart disease. Circulation 2002; vol. 106: pp. 1333-1341; entire document.

Makarenko, I et al. Passive stiffness changes caused by upregulation of compliant titin isoforms in human dilated cardiomyopathy hearts. Circ Res 2004; vol. 95: pp. 708-716; entire document.

Van Heerebeek, L et al. Myocardial structure and function differ in systolic and diastolic heart failure. Circulation 2006; vol. 113: pp. 1966-1973; entire document.

Karsdal, MA et al. Biochemical markers and the FDA critical Path: how biomarkers may contribute to the understanding of pathophysiology and provide unique and necessary tools for drug development. Biomarkers 2009; vol. 14: pp. 181-202; entire document.

Vassiliadis, E et al. Immunological detection of the type V collagen propeptide fragment, PVCP-1230, in connective tissue remodeling associated with liver fibrosis. Biomarkers 2011; vol. 16: pp. 426-433; entire document.

Vassiliadis, E et al. Measurement of CO3-610, a potential liver biomarker derived from matrix metalloproteinase-9 degradation of collagen type III, in a rat model of reversible carbon-tetrachloride-induced fibrosis. Biomarker Insights 2011; vol. 6: pp. 1-10; entire document.

Vassiliadis, E et al. Measurement of matrix metalloproteinase 9-mediated collagen type III degradation fragment as a marker of skin fibrosis. BMC Dermatol 2011; vol. 11: 6; entire document.

Veidal, SS et al. Procollagen type I N-terminal propeptide (PINP) is a marker for fibrogenesis in bile duct ligation-induced fibrosis in rats. Fibrogenesis Tissue Repair 2010; vol. 3: 5; entire document.

Barascuk, N et al. A novel assay for extracellular matrix remodeling associated with liver fibrosis: an enzyme-linked immunosorbent assay (ELISA) for a MMP-9 proteolytically revealed neo-epitope of type III collagen. Clin Biochem 2010; vol. 43: pp. 899-904; entire document.

Zhen, EY et al. Characterization of metalloprotease cleavage products of human articular cartilage. Arthritis Rheum 2008; vol. 58: pp. 2420-2431; entire document.

Johnson, JL et al. Divergent effects of matrix metalloproteinases 3, 7, 9, and 12 on atherosclerotic plaque stability in mouse brachiocephalic arteries. Proc Natl Acad Sci U S A 2005; 102: pp. 15575-15580; entire document.

Bang, M-L et al. The complete gene sequence of titin, expression of an unusual ~700 kDa titin isoform and its interaction with obscurin identify a novel Z-line to I-band linking system. Circ Res 2001; vol. 89: pp. 1065-1072; entire document.

Musco, G et al. Dissecting titin into its structural motifs: identification of an alpha helix near the N-terminus. Biochemistry 1995; vol. 34: pp. 553-561; entire document.

Combet, C et al. NPS@: network protein sequence analysis. Trends Biochem Sci 2000; vol. 25: pp. 147-150; entire document.

Gefter, ML et al. A simple method for polyethylene glycol-promoted hybridization of mouse myeloma cells. Somatic Cell Genet 1977; vol. 3: pp. 231-236; entire document.

Munoz-Luque, J et al. Regression of fibrosis after chronic stimulation of cannabinoid CB2 receptor in cirrhotic rats. J Pharmacol Exp Ther 2008; vol. 324(2): pp. 475-483; entire document.

\* cited by examiner

IN VITRO ASSESSMENT OF CARDIOVASCULAR EVENTS BY ASSAY FOR NEO-EPTITOPES OF TITIN PROTEIN

The present invention relates to assays for biomarkers useful for assessment of cardiovascular events, including but not limited to Acute Myocardial Infarction (AMI), high coronary calcification, and symptomatic non AMI. In particular, according to the present invention, biomarkers relating to degradation fragments of Titin are found to be useful.

Titin, also known as connectin, is a sarcomeric protein expressed in cardiac and skeletal muscle. It is the largest known mammal protein, having a size that can reach up to 3700 kDa[1]. Its main function and one that is well described is to act as a long molecular spring by restoring passive tension during myocardial stretch[2-4]. Titin has two isoforms that are co-expressed in the sarcomere, the N2A which is the larger of the two and is found in both skeletal and myocardial muscle, and the N2B isoform which is smaller, stiffer and is solely found in cardiac muscle[1,5-7]. Due to the different stiffness properties of the isoforms of Titin it has been proposed that the adaptive or maladaptive ratio alteration between the two isoforms, in synergy with their corresponding kinase region, during pathologic events could be responsible for affecting the myocardial contractile properties[3,5,8-12]. Isoform modifications and ratio alterations have been first described in animal models while clinical studies have also reported isoform shifts during dilated cardiomyopathy (DCM), aortic stenosis (AS), diastolic heart failure (DHF) and ischemic heart disease (IHD)[11,13-16]. The main limitation of Titin relevant studies lies on the available methods for detecting and quantifying Titin isoform levels, which are either based on methods that are not sensitive enough such as immunoblotting and gel electrophoresis or techniques which can provide higher sensitivity such as quantitative RT-PCR but can only provide information about the total amount of Titin isoform levels. All of these methods rely on invasive means of tissue collection and identification. Low sensitivity and specificity might contribute to the poor utilisation of these methods as diagnostic or prognostic biomarkers and restrain the correlation of Titin isoform levels with functional studies. In contrast, we discovered according to the present invention that detection of specific degradation fragments of Titin has excellent clinical utility in a number of important clinical situations.

Extracellular matrix (ECM) components are degraded by a number of different proteases including matrix metalloproteinases (MMPs). MMP derived degradation of proteins generates specific cleavage sites/fragments which in turn produce new epitopes. We have previously described that neo epitopes may have potential utility as biomarkers of unbalanced ECM remodeling in a number of different pathologies and can be measured in an array of biological fluids such as serum, plasma and urine[17-22]. A key benefit of this approach is that it is a non-invasive method of measuring specific neo epitopes that represent a unique 'fingerprint' of the proteolytic cleavage of the protein and directly reflect specific tissue turnover in both physiology and pathology.

Accordingly, the present invention now provides in a first aspect a method of bioassay for the quantification of peptide fragments comprising a neo-epitope formed in by cleavage of a titin protein by a proteinase, said method comprising contacting a sample comprising said peptide fragments with an immunological binding partner having specific binding affinity for a said neo-epitope and determining the level of binding of said immunological binding partner to peptide fragments in said sample.

Figure 1:
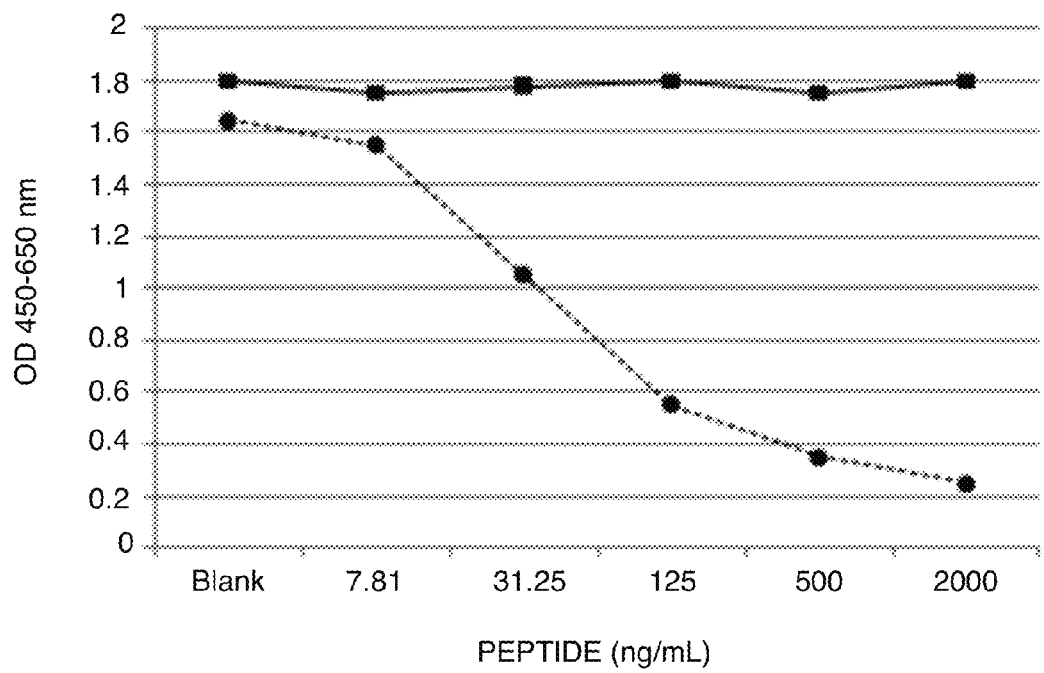
FIG. 1 shows the reactivity of a monoclonal antibody of the invention to target peptide.

Titin proteins include all isoforms of titin, including each of those described above. The titin fragments detected may be in samples derived from any mammalian, for instance a rodent (including particularly mice and rats), dogs, and primates, including monkeys. However, the samples are preferably from a human. Similarly the titin sequences on which the assays are based may come from any of these sources. Generally, the fragments detected will be formed in nature and will be naturally occurring in said sample.

Said immunological binding partner may have specific binding affinity for peptide fragments comprising a C-terminal neo-epitope of said titin protein or for peptide fragments comprising an N-terminal neo-epitope of said titin protein.

Said immunological binding partner may have specific binding affinity for a peptide fragment which comprises a neo-epitope formed by cleavage of a titin protein by a protease giving any one of the following partial sequences of titin:

```
                                          SEQ ID NO: 1
             13519' ↓GEYVCDCGTD '13528

SEQ ID NO: 2
             13532' NVTVEARLIK↓ '13542

SEQ ID NO: 3
             13543' ↓VEKPLYGVEV '13553
```

Said immunological binding partner may have specific binding affinity for either of the following sequences at the N terminal of a peptide:

```
                                          SEQ ID NO: 4
                    13519' ↓GEYVCD

SEQ ID NO: 5
                    13543' ↓VEKPLY
``` or with the following sequence at the C-terminal of a peptide:

```
                                          SEQ ID NO: 6
                       EARLIK↓ '13542
```

Said immunological binding partner may preferably have specific binding affinity for the following sequence at the C terminal of a peptide: NVTVEARLIK↓, '13542.

Preferably, said immunological binding partner is a monoclonal antibody or a fragment of a monoclonal antibody having specific binding affinity.

Said method is preferably conducted as a competition immunoassay in which said immunological binding partner and a competition agent are incubated in the presence of said sample and the competition agent competes with the peptide fragments in the sample to bind to the immunological binding partner. Optionally, said competition agent is a synthetic peptide or is a purified native peptide formed by cleavage of the protein from which said epitope comes so as to reveal said neo-epitope.

The sample is preferably a sample of urine, serum, blood, plasma, or saliva. Included in the invention are methods in which the sample is a patient derived sample, said method further comprising comparing the determined level of said binding of said peptide fragments with values characteristic of (a) comparable healthy individuals and/or (b) a pathological cardiac condition.

In a further aspect, the invention includes an immunological binding partner against a C-terminal or N-terminal neo-epitope formed by proteinase cleavage of a titin protein.

The immunological binding partner may be specifically immunoreactive with the N-terminal of either of the amino acid sequences:

13519' ↓GEYVCD

13543' ↓VEKPLY or with the C-terminal of the amino acid sequence:

EARLIK↓ '13542

The immunological binding partner may be a monoclonal antibody or a binding fragment thereof.

The invention includes in a further aspect a cell line producing a monoclonal antibody described above.

In a further aspect, the invention provides a peptide comprising a C-terminal or N-terminal neo-epitope formed by cleavage of a titin protein by a protease in any one of the partial sequences of said proteins set out above. The peptide may be conjugated as a hapten to a carrier for producing an immune response to said peptide, or immobilised to a solid surface or conjugated to a detectable marker for use in an immunoassay.

In a further aspect, the invention provides an isolated nucleic acid molecule coding for a peptide comprising a C-terminal or N-terminal neo-epitope formed by cleavage of a said protein by a protease in any one of the partial sequences of said proteins set out above.

In a still further aspect, the invention provides a vector comprising a nucleic acid sequence comprising an expression signal and a coding sequence which codes for the expression of a peptide comprising a C-terminal or N-terminal neo-epitope formed by cleavage of a said protein by a protease in any one of the partial sequences of said proteins set out above.

In a still further aspect, the invention provides a host cell transformed with a vector as described above and expressing a said peptide.

In a still further aspect, the invention provides an immunoassay kit comprising an immunological binding partner as described above, and a competition agent which binds said immunological binding partner, and optionally one or more of a wash reagent, a buffer, a stopping reagent, an enzyme label, an enzyme label substrate, calibration standards, an anti-mouse antibody and instructions for conducting an assay using said kit.

During digestion of human tissue with an array of exogenous metalloproteases, a large number of proteolyzed peptide products were identified using mass spectrometry[23]. Among these, a Titin specific fragment 12670' NVTVEARLIK 12679' was identified to be MMP12 cleavage specific. Proteomic analysis revealed that the sequence is unique for the N2B Titin isoform and homologous to human and mouse. Even though at least in murine models MMP12 has been implicated in cardiovascular events such as atherogenesis, the only MMP previously described to have an effect on Titin degradation in relevant bibliography is MMP2 located in the Z-disk region of cardiac sarcomere, contributing to Titin degradation in ischemic and reperfusion related events[24,25]. Due to our mass spectrometry derived finding, we hypothesized that MMP12 may be a more active participant in related pathologic events than previously described and we set out with the hypothesis that the MMP12 specific fragment of the N2B isoform of Titin identified with mass spectrometry could be potentially useful for monitoring pathologic cardiovascular events.

According to the present invention, the following peptide sequences and cleavage sites are useful;

Protease Cleavage sites marked ↓

MMP12 13519' ↓GEYVCDCGTD '13528

MMP12 13532' NVTVEARLIK↓ '13542

MMP12 13543' ↓VEKPLYGVEV '13553

The present invention will be further described and illustrated by the following examples in which reference is made to the accompanying drawings.

EXAMPLE 1

Development of Monoclonal Antibodies to Titin Fragments

All reagents used for experiments were standard high-quality chemicals from Merck (Whitehouse Station, N.J., USA) and Sigma Aldrich (St. Louis, Mo., USA). The synthetic peptides used for monoclonal antibody production were purchased from the Chinese Peptide Company, Beijing, China.

Selection of Peptide for Immunization

The sequence of the peptide selected for the assay was chosen on the basis of mass spectrometry performed on human tissue[23]. Peptide fragments were identified using Uniprot (accession number C0JYZ2). The first 10 amino acids of each free end of the sequences identified were regarded as a target sequences. All relevant sequences were analyzed for homology and then blasted for homology using the CHECK XX NPS@: network protein sequence analysis[28]. The sequence NVTVEARLIK located between amino acid position 12670' and 12679' (Titin) was selected as immunogen. The sequence was identified by Uniprot and PBIL network protein sequence analysis as being unique to human and mouse Titin. The selected sequence was also found to be present in 6 out of 8 Titin isoforms produced by alternative splicing. These were, isoforms 3 (small cardiac N2-B), 7 (cardiac novex-2) and 8 (cardiac novex-1) that are known to present in cardiac muscle (Uniprot accession numbers Q8WZ42-3, Q8WZ42-7 and Q8WZ42-8) and isoforms 2, 4 and 5 (Uniprot accession numbers Q8WZ42-2, Q8WZ42-4 and Q8WZ42-5)[26,27].

Immunization Procedure

Six 4-6 week old Balb/C mice were immunized subcutaneously in the abdomen with 200 µL emulsified antigen (50 µg per immunization), using Freund's incomplete adjuvant (KLH-CGG-NVTVEARLIK SEQ ID NO: 7). Immunizations were performed at two-week intervals until stable titer levels were obtained. At each bleeding, the serum antibody titer was measured and the mice with the highest antibody titer and best reactivity towards serum and urine were selected for fusion. The selected mice were boosted intravenously with 50 µg immunogen in 100 µL 0.9% sodium chloride solution three days before surgical removal of the spleen for cell fusion.

Fusion and Antibody Screening

The fusion procedure has been described elsewhere[29]. Briefly, mouse spleen cells were fused with SP2/0 myeloma fusion partner cells. The hybridoma cells were cloned using a limiting dilution method and transferred into 96-well microtiter plates for further growth. Standard limited dilution was used to promote monoclonal growth. Supernatants were screened using an indirect ELISA, while the biotinylated peptide Biotin-CGG-NVTVEARLIK was used as a catcher peptide on streptavidin-coated microtitre plates.

Characterization of Clones

Native reactivity and peptide binding of the monoclonal antibodies in human serum, plasma and urine was evaluated using a preliminary ELISA with a 10 ng/mL biotinylated peptide coater on a streptavidin-coated microtitre plate and the supernatant from the growing monoclonal hybridoma. Clone specificity was tested against a free peptide (NVTVEARLIK) and a non-sense peptide. Isotyping of the monoclonal antibodies was performed using the Clonotyping System-HRP kit, cat. 5300-05 (Southern Biotech, Birmingham, Ala., USA). The selected clones were purified using Protein G columns according to the manufacturer's instructions and dialysed (GE Healthcare Life Science, Little Chalfont, Buckinghamshire, UK).

In FIG. 1 the reactivity of a monoclonal antibody against the target sequence NVTVEARLIK (circles, dashed line) is compared to the de-selection (and C-terminally elongated) sequence NVTVEARLIKV (square, solid line) (SEQ ID NO: 8). The data clearly demonstrate a strong reactivity to the target sequence NVTVEARLIK with no detectable binding to the elongated peptide. These data suggest a strong binding affinity with the sequence having a free C-terminal lysine residue, i.e. the neo-epitope specificity of the monoclonal antibody is confirmed.

EXAMPLE 2

MMP12 Titin Assay Protocol

The following competitive ELISA protocol was optimised for use with the MMP12 Titin monoclonal antibody. The selected monoclonal antibodies were labelled with horseradish peroxidase (HRP) using the Lightning-Link Horseradish Peroxidase (HRP) antibody labelling kit according to the manufacturer's instructions (Innovabioscience, Babraham, Cambridge, UK). A 96-well streptavidin plate (Roche diagnostics, Basel, Switzerland) was coated with 6.8 ng of the biotinylated synthetic peptide, Biotin-CGG-NVTVEARLIK, dissolved in assay buffer 25 mM Tris BTB and incubated for 30 minutes at 4° C. 20 µL of the peptide calibrator or sample were added to appropriate wells, followed by 100 µL of 280 ng conjugated monoclonal antibody and incubated for 1 hour at 4° C. Finally, 100 µL tetramethyl benzinidine (TMB) (Kem-En-Tec cat. 438OH, Taastrup, Denmark) was added, and the plate was incubated for 15 minutes at 20° C. in the dark. All the above incubation steps included shaking at 300 rpm. After each incubation step the plate was washed five times in washing buffer (20 mM Tris, 50 mM NaCl, pH 7.2). The TMB reaction was stopped by adding 100 µL of stopping solution (1% HCl) and measured at 450 nm with 650 nm as the reference. A calibration curve was plotted using a 4-parametric mathematical fit model with a starting concentration of 200 ng for the standard peptide following a 2-fold dilution.

Figure 2:
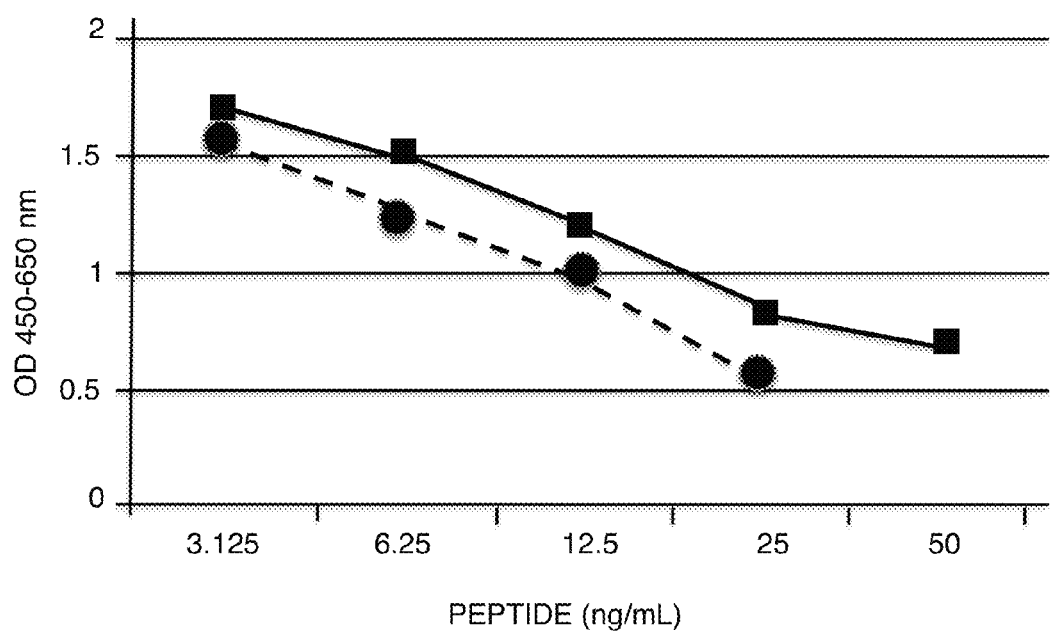
FIG. 2 shows the reactivity of the monoclonal antibody to human serum and urine samples.

In FIG. 2 the reactivity to titin fragments present in human serum is demonstrated. A human serum sample obtained from an individual with AMI was diluted 2-fold and incubated in the MMP12 Titin Elisa described above. The similarity of the curve obtained with human serum and the standard curve suggest that the affinity of the monoclonal antibody is similar against the synthetic peptide NVTVEARLIK and the fragments present in human serum.

EXAMPLE 3

Figure 3:
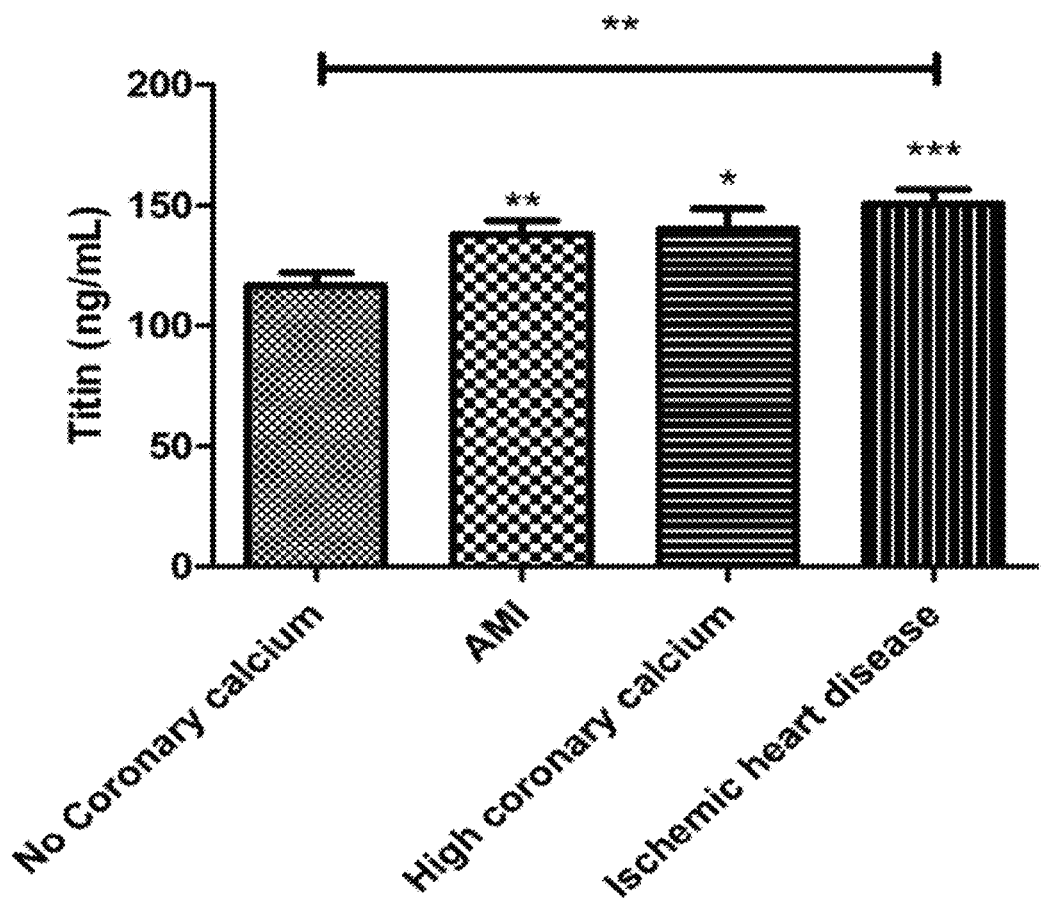
FIG. 3 shows measurements of titin fragment content in human serum from control patients and patients suffering from cardiac diseases.

Assessment of Serum Samples from Subjects with Cardiovascular Events in the MMP12 Titin ELISA Serum from subjects respectively diagnosed with Acute Myocardial Infarction (AMI), high coronary calcification, and symptomatic non AMI were tested in the MMP12 Titin ELISA and compared to healthy controls (FIG. 3).

A statistically significant increase of the marker was measured for all three patient groups. Mean level of controls was measured to be 116.6 ng/ml. MMP12 Titin levels were elevated in all patient groups examined, AMI patients mean value 137.9 ng/ml ($P<0.05$), Patients with high coronary calcification 140 ng/ml ($P<0.05$) and Ischemic heart disease 150.6 ng/ml ($P<0.05$) (FIG. 3).

Biochemical markers consisting of protein fragments from ECM degradation may be informative of disease pathology and progression, which in turn may be useful for diagnostic and prognostic purposes. These markers could potentially detect changes resulting from intervention strategies and serve as surrogate markers of drug efficacy[30].

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

REFERENCE LIST (1) LeWinter M M, Wu Y, Labeit S, Granzier H. Cardiac titin: structure, functions and role in disease. Clin Chim Acta 2007 January; 375(1-2):1-9.
(2) LeWinter M M, Granzier H. Cardiac titin: a multifunctional giant. Circulation 2010 May 18; 121(19):2137-45.
(3) Wu Y, Bell S P, Trombitas K et al. Changes in titin isoform expression in pacing-induced cardiac failure give rise to increased passive muscle stiffness. Circulation 2002 Sep. 10; 106(11):1384-9.
(4) Sutko J L, Publicover N G, Moss R L. Titin: an elastic link between length and active force production in myocardium. Circulation 2001 Oct. 2; 104(14):1585-7.
(5) Jaber W A, Maniu C, Krysiak J et al. Titin isoforms, extracellular matrix, and global chamber remodeling in experimental dilated cardiomyopathy: functional implications and mechanistic insight. Circ Heart Fail 2008 September; 1(3):192-9.
(6) Hein S, Gaasch W H, Schaper J. Giant molecule titin and myocardial stiffness. Circulation 2002 Sep. 10; 106(11): 1302-4.

(7) LeWinter M M. Titin isoforms in heart failure: are there benefits to supersizing? Circulation 2004 Jul. 13; 110(2): 109-11.
(8) Linke W A. Sense and stretchability: the role of titin and titin-associated proteins in myocardial stress-sensing and mechanical dysfunction. Cardiovasc Res 2008 Mar. 1; 77(4):637-48.
(9) Chaturvedi R R, Herron T, Simmons R et al. Passive stiffness of myocardium from congenital heart disease and implications for diastole. Circulation 2010 Mar. 2; 121 (8):979-88.
(10) Thijssen V L, Borgers M, Lenders M H et al. Temporal and spatial variations in structural protein expression during the progression from stunned to hibernating myocardium. Circulation 2004 Nov. 23; 110(21):3313-21.
(11) Nagueh S F, Shah G, Wu Y et al. Altered titin expression, myocardial stiffness, and left ventricular function in patients with dilated cardiomyopathy. Circulation 2004 Jul. 13; 110(2):155-62.
(12) Peng J, Raddatz K, Molkentin J D et al. Cardiac hypertrophy and reduced contractility in hearts deficient in the titin kinase region. Circulation 2007 Feb. 13; 115(6):743-51.
(13) Linke W A. Titin stiffness in heart disease. Circulation 2003 Mar. 25; 107(11):e73.
(14) Neagoe C, Kulke M, del M F et al. Titin isoform switch in ischemic human heart disease. Circulation 2002 Sep. 10; 106(11):1333-41.
(15) Makarenko I, Opitz C A, Leake M C et al. Passive stiffness changes caused by upregulation of compliant titin isoforms in human dilated cardiomyopathy hearts. Circ Res 2004 Oct. 1; 95(7):708-16.
(16) van H L, Borbely A, Niessen H W et al. Myocardial structure and function differ in systolic and diastolic heart failure. Circulation 2006 Apr. 25; 113(16):1966-73.
(17) Karsdal M A, Henriksen K, Leeming D J et al. Biochemical markers and the FDA Critical Path: how biomarkers may contribute to the understanding of pathophysiology and provide unique and necessary tools for drug development. Biomarkers 2009 May; 14(3):181-202.
(18) Vassiliadis E, Veidal S S, Simonsen H et al. Immunological detection of the type V collagen propeptide fragment, PVCP-1230, in connective tissue remodeling associated with liver fibrosis 1. Biomarkers 2011 May 25.
(19) Vassiliadis E, Larsen D V, Clausen R E et al. Measurement of CO3-610, a Potential Liver Biomarker Derived from Matrix Metalloproteinase-9 Degradation of Collagen Type III, in a Rat Model of Reversible Carbon-Tetrachloride-Induced Fibrosis 4. Biomark Insights 2011; 6:49-58.
(20) Vassiliadis E, Veidal S S, Barascuk N et al. Measurement of matrix metalloproteinase 9-mediated collagen type III degradation fragment as a marker of skin fibrosis 5. BMC Dermatol 2011; 11:6.
(21) Veidal S S, Vassiliadis E, Bay-Jensen A C, Tougas G, Vainer B, Karsdal M A. Procollagen type 1 N-terminal propeptide (PIMP) is a marker for fibrogenesis in bile duct ligation-induced fibrosis in rats. Fibrogenesis Tissue Repair 2010; 3(1):5.
(22) Barascuk N, Vassiliadis E, Larsen L et al. Development and validation of an enzyme-linked immunosorbent assay for the quantification of a specific MMP-9 mediated degradation fragment of type III collagen-A novel biomarker of atherosclerotic plaque remodeling. Clin Biochem 2011 July; 44(10-11):900-6.
(23) Zhen E Y, Brittain I J, Laska D A et al. Characterization of metalloprotease cleavage products of human articular cartilage. Arthritis Rheum 2008 August; 58(8):2420-31.
(24) Ali M A, Cho W J, Hudson B, Kassiri Z, Granzier H, Schulz R. Titin is a target of matrix metalloproteinase-2: implications in myocardial ischemia/reperfusion injury. Circulation 2010 Nov. 16; 122(20):2039-47.
(25) Johnson J L, George S J, Newby A C, Jackson C L. Divergent effects of matrix metalloproteinases 3, 7, 9, and 12 on atherosclerotic plaque stability in mouse brachiocephalic arteries. Proc Natl Acad Sci USA 2005 Oct. 25; 102(43):15575-80.
(26) Bang M-L, Centner R, Formoff F et al. The complete gene sequence of titin, expression of an unusual ~700 kDa titin isoform and its interaction with obscurin identify a novel Z-line to I-band linking system. Circ Res 2001; 89:1065-72.
(27) Musco G, Tziatzos C, Schuck P, Pastore A. Dissecting titin into its structural motifs: identification of an alpha helix near the N-terminus. Biochemistry 1995; 34:553-61.
(28) Combet C, Blanchet C, Geourjon C, Deleage G. NPS@: network protein sequence analysis. Trends Biochem Sci 2000 March; 25(3):147-50.
(29) Gefter M L, Margulies D H, Scharff M D. A simple method for polyethylene glycol-promoted hybridization of mouse myeloma cells. Somatic Cell Genet 1977 March; 3(2):231-6.
(30) Munoz-Luque J, Ros J, Fernandez-Varo G et al. Regression of fibrosis after chronic stimulation of cannabinoid CB2 receptor in cirrhotic rats. J Pharmacol Exp Ther 2008 February; 324(2):475-83.

The invention claimed is:

1. A method of assessing cardiovascular events comprising:
   obtaining a biofluid sample from a patient;
   conducting an immunoassay to measure fragments of a titin protein having an N- or a C-terminal neo-epitope formed by cleavage of said titin protein by a proteinase, said fragments being naturally present in said sample;
   wherein said immunoassay is conducted by a method comprising:
      contacting the fragments of said titin protein having said N- or C-terminal neo-epitope that are naturally present in said sample with an immunological binding partner having specific binding affinity for said N- or C-terminal neo-epitope but not reactive with intact titin and determining the level of binding of said immunological binding partner to said N- or C-terminal neo-epitope to measure therein fragments comprising said neo-epitope,
   wherein said immunological binding partner is raised against a synthetic peptide corresponding to the N- or the C-terminal neo-epitope amino acid sequence formed by cleavage of the titin protein by a proteinase and specifically binds the neo-epitope comprised in said N- or C-terminal terminal amino acid sequence, said N- or C-terminal amino acid sequence selected from the group consisting of:

↓GEYVCDCGTD                    SEQ ID NO: 1

NVTVEARLIK↓                    SEQ ID NO: 2

↓VEKPLYGVEV                    SEQ ID NO: 3 and,
   associating an elevation of said measure in said patient above a normal level with the presence or extent of a cardiovascular event.

2. A method as claimed in claim 1, wherein said immunological binding partner has specific binding affinity for said fragments comprising a C-terminal neo-epitope of said titin protein.

3. A method as claimed in claim 1, wherein said immunological binding partner has specific binding affinity for said fragments comprising an N-terminal neo-epitope of said titin protein.

4. A method as claimed in claim 1, wherein said immunological binding partner has specific binding affinity for either of the following sequences at the N terminal of a peptide:

↓GEYVCD                        SEQ ID NO: 4

↓VEKPLY                        SEQ ID NO: 5 or with the following sequence at the C-terminal of a peptide:

EARLIK↓ '13542.                SEQ ID NO: 6

5. A method as claimed in claim 4, wherein said immunological binding partner has specific binding affinity for the following sequence at the C terminal of a peptide: NVTVEARLIK SEQ ID NO: 2.

6. A method as claimed in claim 1, wherein said immunological binding partner is a monoclonal antibody or a fragment of a monoclonal antibody having specific binding affinity.

7. A method as claimed in claim 1, wherein said method is conducted as a competition immunoassay in which said immunological binding partner and a competition agent are incubated in the presence of said sample and the competition agent competes with the fragments of said titin protein having said N- or C-terminal neo-epitope formed by cleavage of said titin protein by a proteinase present in the sample to bind to the immunological binding partner.

8. A method as claimed in claim 7, wherein said competition agent is a synthetic peptide or is a purified native peptide formed by cleavage of the protein from which said epitope comes so as to reveal said neo-epitope.

9. A method as claimed in claim 1, wherein the sample is a sample of urine, serum, blood, plasma, or saliva.

10. A method as claimed in claim 1, wherein the sample is a patient derived sample, said method further comprising comparing the determined level of said binding of said fragments with values characteristic of (a) comparable healthy individuals and/or (b) a pathological cardiac condition.

* * * * *

SEQUENCE LISTING

```
<160> NUMBER OF SEQ ID NOS: 8

<210> SEQ ID NO 1
<211> LENGTH: 10
<212> TYPE: PRT
<213> ORGANISM: Homo sapiens
<220> FEATURE:
<221> NAME/KEY: PEPTIDE
<223> OTHER INFORMATION: Titin protein cleavage fragment

<400> SEQUENCE: 1

Gly Glu Tyr Val Cys Asp Cys Gly Thr Asp
1               5                   10
```

```
<210> SEQ ID NO 2
<211> LENGTH: 10
<212> TYPE: PRT
<213> ORGANISM: Homo sapiens
<220> FEATURE:
<221> NAME/KEY: PEPTIDE
<223> OTHER INFORMATION: Titin protein cleavage fragment

<400> SEQUENCE: 2

Asn Val Thr Val Glu Ala Arg Leu Ile Lys
1               5                   10

<210> SEQ ID NO 3
<211> LENGTH: 10
<212> TYPE: PRT
<213> ORGANISM: Homo sapiens
<220> FEATURE:
<221> NAME/KEY: PEPTIDE
<223> OTHER INFORMATION: Titin protein cleavage fragment

<400> SEQUENCE: 3

Val Glu Lys Pro Leu Tyr Gly Val Glu Val
1               5                   10

<210> SEQ ID NO 4
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Titin protein cleavage
      fragment

<400> SEQUENCE: 4

Gly Glu Tyr Val Cys Asp
1               5

<210> SEQ ID NO 5
<211> LENGTH: 6
<212> TYPE: PRT
<213> ORGANISM: Homo sapiens
<220> FEATURE:
<221> NAME/KEY: PEPTIDE
<223> OTHER INFORMATION: N-terminal sequence of Titin protein cleavage
      fragment

<400> SEQUENCE: 5

Val Glu Lys Pro Leu Tyr
1               5

<210> SEQ ID NO 6
<211> LENGTH: 6
<212> TYPE: PRT
<213> ORGANISM: Homo sapiens
<220> FEATURE:
<221> NAME/KEY: PEPTIDE
<223> OTHER INFORMATION: C-terminal sequence of Titin protein cleavage
      fragment

<400> SEQUENCE: 6

Glu Ala Arg Leu Ile Lys
1               5

<210> SEQ ID NO 7
<211> LENGTH: 13
<212> TYPE: PRT
<213> ORGANISM: Artificial sequence
<220> FEATURE:
<223> OTHER INFORMATION: immunogenic peptide
```

```
<400> SEQUENCE: 7

Cys Gly Gly Asn Val Thr Val Glu Ala Arg Leu Ile Lys
1               5                   10

<210> SEQ ID NO 8
<211> LENGTH: 11
<212> TYPE: PRT
<213> ORGANISM: Artificial sequence
<220> FEATURE:
<223> OTHER INFORMATION: deselection non-sense peptide

<400> SEQUENCE: 8

Asn Val Thr Val Glu Ala Arg Leu Ile Lys Val
1               5                   10
```